United States Patent [19]

Hagen

[11] Patent Number: 5,424,481
[45] Date of Patent: Jun. 13, 1995

[54] PREPARATION OF METHYLSULFONYLBENZOIC ACIDS

[75] Inventor: Helmut Hagen, Frankenthal, Germany

[73] Assignee: BASF Aktiengesellschaft, Ludwigshafen, Germany

[21] Appl. No.: 135,414

[22] Filed: Oct. 13, 1993

[30] Foreign Application Priority Data

Oct. 19, 1992 [DE] Germany .................. 42 35 155.3

[51] Int. Cl.⁶ ............................................ C07C 51/16
[52] U.S. Cl. .................................... 562/410; 562/411; 562/412; 562/429; 562/430
[58] Field of Search ............... 562/410, 411, 412, 429, 562/430

[56] References Cited

U.S. PATENT DOCUMENTS 5,055,605 10/1991 Ludvik .
5,196,573 3/1993 Patsch et al. .
5,198,575 3/1993 Hagen et al. .

FOREIGN PATENT DOCUMENTS 0460544 12/1991 European Pat. Off. .
WO90/06301 6/1990 WIPO .
WO90/06302 6/1990 WIPO .

*Primary Examiner*—José G. Dees
*Assistant Examiner*—Samuel Barts
*Attorney, Agent, or Firm*—Oblon, Spivak, McClelland, Maier, & Neustadt

[57] ABSTRACT

A process for preparing methylsulfonylbenzoic acids comprises oxidizing the corresponding methylsulfonyltoluenes with nitric acid and air in sulfuric acid in the presence of vanadium or cobalt compounds.

4 Claims, No Drawings

PREPARATION OF METHYLSULFONYLBENZOIC ACIDS

The present invention relates to a novel process for preparing methylsulfonylbenzoic acids by oxidation of the corresponding methylsulfonyltoluenes.

EP-A-460 544 discloses the preparation of hydroxysulfonylanthranilic acids by oxidation of the corresponding nitrotoluenes.

It is an object of the present invention to provide a novel process for preparing methylsulfonylbenzoic acids. The novel process shall use methylsulfonyltoluenes as starting materials and shall give the target products in high yield and purity by oxidation of the toluenic methyl group.

We have found that this object is achieved by a process for preparing methylsulfonylbenzoic acids of the formula I

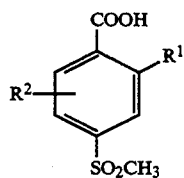

where
$R^1$ is hydrogen, nitro, halogen or hydroxysulfonyl, and
$R^2$ is hydrogen, nitro or halogen, which comprises oxidizing methylsulfonyltoluenes of the formula II

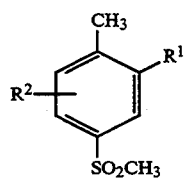

where $R^1$ and $R^2$ are each as defined above, in sulfuric acid with nitric acid and air in the presence of vanadium or cobalt compounds.

$R^1$ and $R^2$ are each for example fluorine, chlorine or bromine.

Suitable vanadium compounds are in particular vanadium(V) compounds, such as vanadium pentoxide and ammonium metavanadate ($NH_4VO_3$). The use of vanadium pentoxide is preferred. Under the reaction conditions the vanadium compounds are generally present in the form of vanadium(V) sulfate.

Suitable cobalt compounds are in particular cobalt(II) compounds, such as cobalt(II) sulfate heptahydrate, cobalt(II) nitrate hexahydrate and cobalt(II) acetate tetrahydrate.

The practice of the process of the invention in the presence of vanadium compounds is preferred.

The process of the invention is carried out in sulfuric acid as the reaction medium. The sulfuric acid used is advantageously from 60 to 80% strength by weight, in particular from 70 to 75% strength by weight. Based on the weight of methylsulfonyltoluene II, the amount of sulfuric acid used is in general from 100 to 1200% by weight, preferably from 500 to 1000% by weight.

The oxidizing agents used are nitric acid and air. The nitric acid used is advantageously from 30 to 100% strength by weight, in particular from 55 to 65% strength by weight.

Based on the weight of methylsulfonyltoluene II, the amount of nitric acid used is in general from 100 to 400% by weight, preferably from 200 to 300% by weight. The nitric acid is metered into the reaction mixture at a uniform rate over the course of the reaction (in general over a period of from 6 to 12 hours).

The air used as a further oxidizing agent besides nitric acid is in general employed at a rate of from 10 to 100 l/h, preferably from 20 to 50 l/h, per l of reactor volume. This rate of passing air into the reaction mixture is maintained throughout the entire course of the reaction.

The vanadium or cobalt compounds are in general employed in a catalytic amount. This means that, based on the weight of methylsulfonyltoluene of the formula II, it is customary to use from 1 to 10% by weight, preferably from 2 to 5% by weight, of a vanadium or cobalt compound.

The novel process is carried out at from 130 to 170° C., preferably at from 145° to 155° C., and in general under atmospheric pressure.

The process of the invention is preferably employed for preparing methylsulfonylbenzoic acids of the formula I where $R^1$ is hydrogen or nitro and $R^2$ is hydrogen.

The novel process is advantageously carried out by introducing a methylsulfonyltoluene II, a vanadium or cobalt compound and the sulfuric acid as initial charge and heating the initial charge to the abovementioned temperature while passing air into it. Then the metered addition of the nitric acid is commenced. It is advantageous to distill dilute (about 20–40% strength by weight) nitric acid out of the reaction mixture at the same time.

After the reaction has ended, the reaction mixture is cooled down and the precipitated methylsulfonylbenzoic acid is filtered off with suction, washed with water and dried.

The starting methylsulfonyltoluenes of the formula II can be prepared in a conventional manner. One possibility is for example to react the corresponding toluenes with methanesulfonyl chloride in a Friedel-Crafts reaction.

However, it is particularly advantageous to combine the process of the invention with the method for preparing methylsulfonyltoluene described in WO 90/06301.

In this case toluenesulfonyl chlorides of the formula III

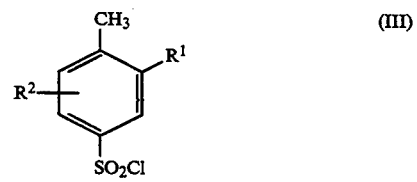

where $R^1$ and $R^2$ are each as defined above, are reduced in aqueous solution with an alkali metal sulfite, in particular sodium sulfite. The resulting alkali metal sulfinate is then alkylated with chloroacetic acid and decarboxylated by heating.

The reduction of the toluenesulfonyl chloride III is carried out in aqueous solution with sodium sulfite in the presence of sodium bicarbonate at from 15° to 30° C.

After an aqueous solution of the sodium salt of chloroacetic acid has been added, the reaction mixture is stirred under reflux for 15-20 hours. Cooling brings down the methylsulfonyltoluene II as a precipitate, which is filtered off with suction and can be used without further purification as a starting material in the process of the invention.

The methylsulfonyltoluenes II used as starting materials for preparing those methylsulfonylbenzoic acids of the formula I where $R^1$ is nitro are advantageously obtained by nitrating the corresponding nitro-free methylsulfonyltoluenes II. Specifically, methylsulfonyltoluene II is nitrated with 50-65% strength by weight nitric acid at 0°-10° C. in concentrated sulfuric acid. After the nitration has ended, the reaction mixture is diluted with water until the sulfuric acid is present as an aqueous sulfuric acid of from 60 to 80% strength by weight, preferably about 70% strength by weight. This mixture can then be used directly for carrying out the process of the invention.

The process of the invention, which can be carried out continuously as well as batchwise, gives the methylsulfonylbenzoic acids of the formula I in a simple manner in high yield and purity.

What is surprising is that, under the conditions of the invention, the methyl group on the ring is oxidized very selectively to the carboxyl group with virtually no attack on the methylsulfonyl group.

The methylsulfonylbenzoic acids obtainable by the novel process are useful intermediates for preparing dyes or active compounds, in particular for preparing herbicides as described for example in U.S. Pat. No. 5,055,605.

Embodiments of the invention will now be more particularly described by way of example.

EXAMPLE 1 a) Preparation of 4-methylsulfonyltoluene 176.4 g of sodium sulfite and 226 g of sodium bicarbonate were dissolved in 1800 ml of water and cooled down to 15° C. 244 g of p-toluenesulfonyl chloride were added at that temperature with thorough stirring. The mixture was additionally stirred for 3 hours at 15° C. and overnight at room temperature. It was then heated to 40° C. and a solution of 175 g of the sodium salt of chloroacetic acid in 400 ml of water was added. The reaction mixture was stirred under reflux for 24 hours. After cooling down to 5°-10° C. the precipitated product was filtered off with suction and dried at 50° C. under reduced pressure, leaving 192.5 g of 4-methylsulfonyltoluene (melting point 83°-86° C).

b) Preparation of 4-methylsulfonyl-2-nitrotoluene 68 g of 4-methylsulfonyltoluene in 400 ml of concentrated sulfuric acid were admixed at 0°-10° C. with a mixture of 80 ml of concentrated sulfuric acid and 31 ml of 65% strength by weight nitric acid. The reaction mixture was stirred at 10° C. for 2 hours and at room temperature for a further 2 hours. It was then poured onto about 1 kg of ice, and the solids were filtered off with suction, washed with water and dried at 50° C. under reduced pressure, to leave 85 g of 4-methylsulfonyl-2-nitrotoluene (melting point 112°-115° C.).

c) Preparation of 4-methylsulfonyl-2-nitrobenzoic acid 45 g of 4-methylsulfonyl-2-nitrotoluene and 1 g of vanadium pentoxide were dissolved in 375 ml of 70% strength by weight sulfuric acid. The reaction mixture was heated to 145° C. while air was passed into it at a rate of 100 l/h. Once at that temperature of 145° C. the metered addition was commenced of 65% strength by weight nitric acid at a rate of 0.25 ml/min. A total of 135 ml of nitric acid were added over 9 hours. At the same time 120 ml of 35% strength by weight nitric acid were distilled out of the reaction mixture. The reaction mixture was then cooled down to 20° C. and the precipitate was filtered off with suction and washed with water. This yielded 44 g (83% of theory) of 4-methylsulfonyl-2-nitrobenzoic acid (melting point 204°-206° C).

EXAMPLE 2

68 g of 4-methylsulfonyltoluene (Example 1a) were nitrated in 400 ml of concentrated sulfuric acid as described in Example 1b.

300 ml of water and 1 g of vanadium pentoxide were added to the reaction mixture, and the mixture was heated to 145° C. while air was passed into it at a rate of 100 l/h. Once at that temperature the metered addition was commenced of 65% strength by weight nitric acid and continued for 9 hours, a total of 270 ml being added.

The reaction mixture was cooled down to room temperature, and the precipitate was filtered off with suction, washed with water and dried.

This yielded 87 g (81% of theory) of 4-methylsulfonyl-2-nitrobenzoic acid (melting point 203°-206° C.).

We claim:

1. A process for preparing a methylsulfonylbenzoic acid of the formula I

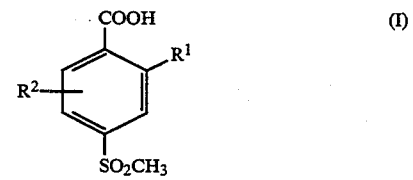

where
$R^1$ is nitro, and
$R^2$ is hydrogen, nitro or halogen, which comprises oxidizing methylsulfonyltoluene of the formula II

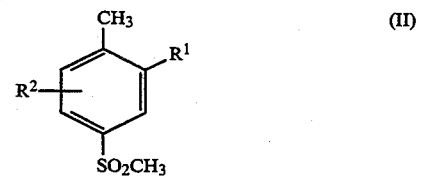

where $R^1$ and $R^2$ are each as defined above, in sulfuric acid with nitric acid and air in the presence of vanadium a or cobalt compound, wherein said air is supplied at a rate of from about 10 to about 100 l/h per l of reactor volume.

2. A process as claimed in claim 1, wherein $R^2$ is hydrogen.

3. A process as claimed in claim 1, wherein the oxidation is carried out in the presence of a vanadium compound.

4. A process as claimed in claim 1, wherein the oxidation is carried out at from 130° to 170° C.

* * * * *